US009332892B2

(12) United States Patent
Hatanaka et al.

(10) Patent No.: US 9,332,892 B2
(45) Date of Patent: May 10, 2016

(54) LIGHT CONVERGING TYPE LIGHT GUIDE UNIT AND LIGHT SOURCE DEVICE USING THE SAME

(71) Applicant: IWASAKI ELECTRIC CO., LTD., Tokyo (JP)

(72) Inventors: Mitsuyuki Hatanaka, Gyoda (JP); Takashi Satou, Gyoda (JP); Nozomu Kajiwara, Gyoda (JP); Takaaki Komiya, Gyoda (JP)

(73) Assignee: IWASAKI ELECTRIC CO., LTD., Tokyo (JP)

( * ) Notice: Subject to any disclaimer, the term of this patent is extended or adjusted under 35 U.S.C. 154(b) by 33 days.

(21) Appl. No.: 14/033,026

(22) Filed: Sep. 20, 2013

(65) Prior Publication Data
US 2014/0112016 A1  Apr. 24, 2014

(30) Foreign Application Priority Data

Oct. 19, 2012  (JP) .................................. 2012-232292

(51) Int. Cl.
*G03B 29/00* (2006.01)
*A61B 1/00* (2006.01)
(Continued)

(52) U.S. Cl.
CPC ............ *A61B 1/00165* (2013.01); *A61B 1/0669* (2013.01); *A61B 1/0684* (2013.01); *A61B 1/07* (2013.01); *F21V 2200/10* (2015.01)

(58) Field of Classification Search
CPC .......... G02B 5/08; G02B 6/0096; F21V 9/01; F21V 13/08; F21V 7/0809; F21S 8/02
USPC ................. 362/574, 296.06, 311.08; 250/343
See application file for complete search history.

(56) References Cited

U.S. PATENT DOCUMENTS 6,108,131 A * 8/2000 Hansen et al. ........... 359/485.05
6,547,400 B1 * 4/2003 Yokoyama .................... 353/98
(Continued)

FOREIGN PATENT DOCUMENTS

JP      09-281413 A      10/1997
JP      2010-161033 A     7/2010
(Continued)

OTHER PUBLICATIONS

Office Action dated Sep. 9, 2014, issued in corresponding Japanese Patent Application No. 2012-232292, with English Translation (7 pages).

*Primary Examiner* — Evan Dzierzynski
*Assistant Examiner* — Matthew Peerce
(74) *Attorney, Agent, or Firm* — Westerman, Hattori, Daniels & Adrian, LLP

(57) ABSTRACT

In a light converging type light guide unit for guiding light emitted from a light source to a light-receiving member having a reflection face extending from a light emission point to at least a place in the neighborhood of a light reception point of the light-receiving member, the reflection face has first and second focal points at which the light emission and reception points are disposed, respectively, and comprises an elliptical reflection face at the side of the light reception point, and a curved surface reflection face that is provided at the side of the light emission point, reflects light of the light source therefrom to the elliptical reflection face and obtains light that travels to the light reception point and is incident to the light reception point at a predetermined incidence angle or less by reflection from the elliptical reflection face.

7 Claims, 10 Drawing Sheets

(51) Int. Cl.
  *A61B 1/06*  (2006.01)
  *A61B 1/07*  (2006.01)

(56) References Cited

U.S. PATENT DOCUMENTS

| | | | |
|---|---|---|---|
| 6,969,177 B2 * | 11/2005 | Li et al. | 362/19 |
| 7,832,878 B2 * | 11/2010 | Brukilacchio et al. | 353/99 |
| 2003/0218802 A1 * | 11/2003 | Kitabayashi | 359/495 |
| 2004/0174709 A1 * | 9/2004 | Buelow et al. | 362/296 |
| 2005/0219478 A1 * | 10/2005 | Yoshii et al. | 353/99 |
| 2006/0114423 A1 * | 6/2006 | Maeda et al. | 353/94 |
| 2006/0164607 A1 * | 7/2006 | Morejon et al. | 353/94 |
| 2007/0152230 A1 * | 7/2007 | Duong et al. | 257/98 |
| 2007/0195278 A1 * | 8/2007 | Yokote et al. | 353/34 |
| 2008/0123056 A1 * | 5/2008 | Matsubara | 353/20 |
| 2009/0066920 A1 * | 3/2009 | Yamagishi et al. | 353/99 |

FOREIGN PATENT DOCUMENTS

| | | |
|---|---|---|
| JP | 2011-200380 A | 10/2011 |
| JP | 2012-105715 A | 6/2012 |

* cited by examiner

LIGHT CONVERGING TYPE LIGHT GUIDE UNIT AND LIGHT SOURCE DEVICE USING THE SAME

INCORPORATION BY REFERENCE

The present application claims priority under 35 U.S.C. §119 to Japanese Patent Application No. 2012-232292 filed on Oct. 19, 2012. The content of the application is incorporated herein by reference in its entirety.

BACKGROUND OF THE INVENTION

1. Field of the Invention

The present invention relates to a light guiding technique for guiding light emitted from a light source to a light receiving member.

2. Related Art

An endoscope has been widely used to observe the inside of a body cavity in a medical field, etc. The endoscope normally has a light guide for guiding illumination light to an observation site to illuminate the observation site, and a light source device for emitting illumination light and making the illuminated light incident to the light guide is known (for example, see JP-A-2012-105715 and JP-A-2011-200380). Furthermore, LED (Light Emitting Diode) which has a large light amount per unit area in spite of a small light emission point has been practically used.

The light source device generally has a light converging optical system for converging light from the light source to the incident face of the light guide. However, use efficiency of light emitted from LED in the light guide is low in the light converging optical system described above, and thus it has been difficult to efficiently use light of LED as illumination light of an endoscope.

SUMMARY OF THE INVENTION

The present invention has been implemented in view of the foregoing description, and has an object to provide a light converging type light guide unit that can enhance use efficiency of light emitted from a light source in a light guide, and a light source device having the light converging type light guide unit.

In order to attain the above object, according to a first aspect of the present invention, in a light converging type light guide unit for guiding light emitted from a light source to a light-receiving member having a reflection face extending from a light emission point of the light source to at least a place in the neighborhood of a light reception point of the light-receiving member, the reflection face has a first focal point at which the light emission point is disposed and a second focal point at which the light reception point is disposed, and comprises an elliptical reflection face at the light reception point side, and a curved surface reflection face that is provided at the light emission point side and configured to reflect light of the light source therefrom to the elliptical reflection face and obtain light that travels to the light reception point and is incident to the light reception point at a predetermined incidence angle or less by reflection from the elliptical reflection face.

In the light converging type light guide unit, the curved surface reflection face is provided to an area of the reflection face in which reflection light deviating from the light reception point of the second focal point would occur due to a size of the light emission point on the assumption that the overall reflection face comprises an elliptical reflection face.

In the light converging type light guide unit, the reflection face is configured to surround an area extending from the light emission point of the light source to at least the place in the neighborhood of the light reception point of the light-receiving member.

In the light converging type light guide unit, an end face of a light guide is disposed at the light reception point, and when a numerical aperture of the light guide is represented by NA, the curved surface reflection face obtains light that travels to the light emission point and is incident to the light emission point at an incidence angle of Arcsin (NA) or less.

The light converging type light guide unit further comprises a dichroic mirror provided on an optical axis of the reflection face, wherein the reflection face has a sub reflection face which is geometrically equivalent to a face of the reflection face that extends from the dichroic mirror to the first focal point, the light emission point of the light source is disposed at a first focal point of the sub reflection face, and light at the sub reflection face side and light at the reflection face side are combined with each other by the dichroic mirror.

According to a second aspect of the present invention, a light source for making light incident to a light guide comprises the light converging type light guide unit described above, and a light source for making light incident to the light converging type light guide unit, wherein an incidence end face of the light guide is disposed at the light reception point of the light-receiving member, and the light converging type light guide unit makes the light of the light source incident to the light guide.

According to the present invention, the elliptical reflection face is formed at the light reception point side of the reflection face whereas the hyperbolic reflection face is formed at the light emission point side of the reflection face. Therefore, even when the light emission point has a size, light reflected at the light emission point side of the reflection face can be efficiently made incident to the light reception point.

Furthermore, the incidence angle to the light reception point can be also controlled for the reflection light reflected in the neighborhood of the light reception point of the elliptical reflection face. Therefore, even when the incidence angle to the light reception point is restricted as in the case of a light guide, light can be made incident to the light emission point at an incidence angle satisfying the above restriction.

DETAILED DESCRIPTION OF THE EMBODIMENTS

Embodiments according to the present invention will be described with reference to the drawings.

Figure 1:
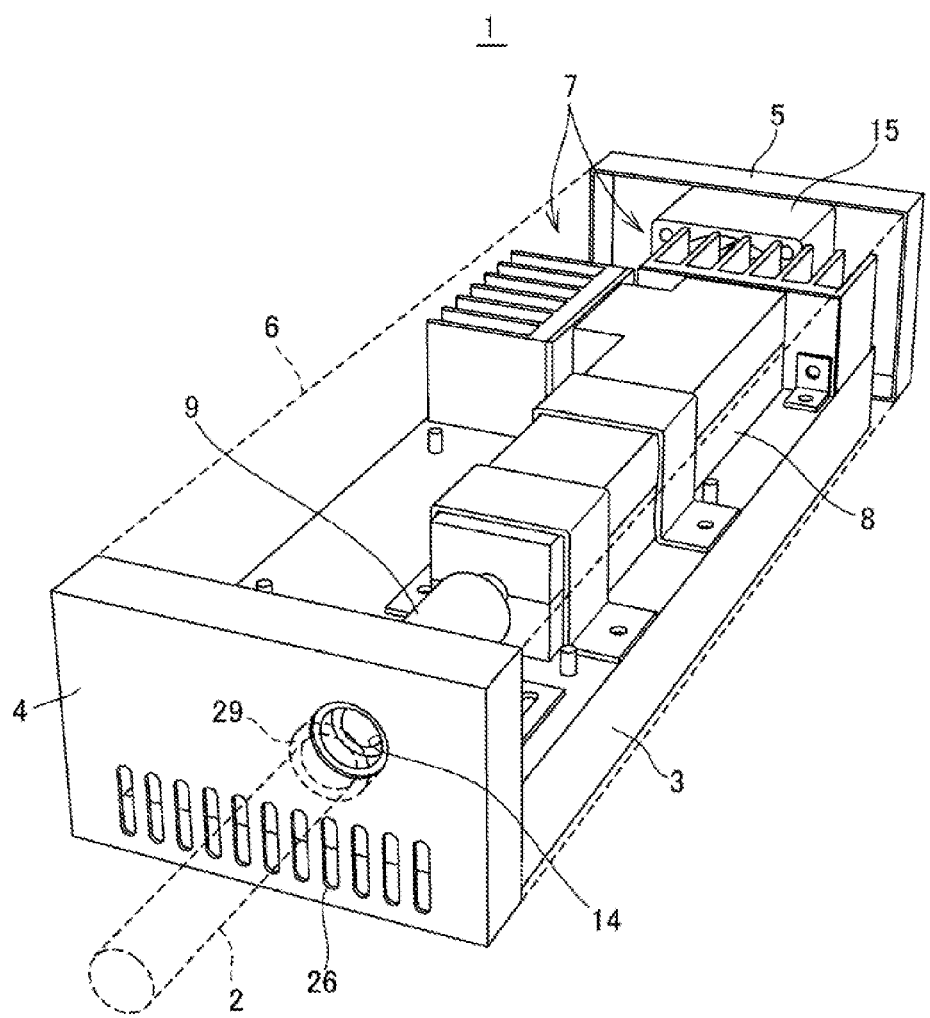
FIG. 1 is a perspective view showing the construction of a light source device according to an embodiment of the present invention.
Figure 2:
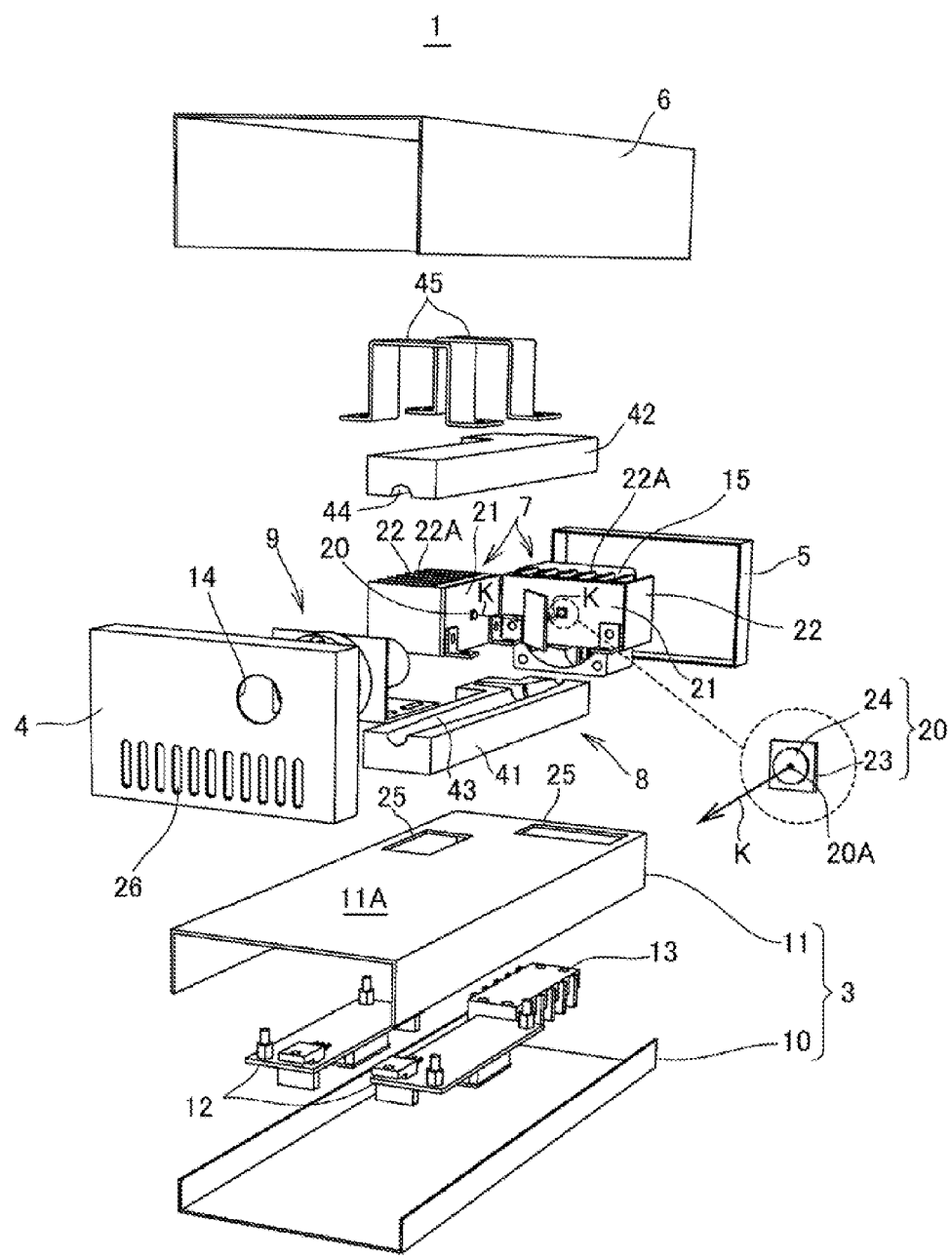
FIG. 2 is an exploded perspective view showing the light source device.

FIG. 1 is a perspective view showing the construction of a light source device 1 according to an embodiment of the present invention, and FIG. 2 is an exploded perspective view showing the light source device 1. In FIG. 1, a cover case 6 is represented by a virtual line to make the internal structure of the light source device 1 be easily understandable.

The light source device 1 is used as a light source for an endoscope having a light guide 2 comprising an elongated light guide member. As shown in FIG. 1, the light source device 1 makes light incident to the light guide 2, and the incident light is guided through the light guide 2 to an observing site of an endoscope and applied to an observation site as illumination light.

As shown in FIGS. 1 and 2, the light source device 1 of this embodiment has a board box 3, a front cover 4, a back cover 5, a cover case 6, two light source units 7, a light converging type light guide unit 8, a holder unit 9 and a heat radiation fan 15.

The board box 3 is designed to have a substantially plate-shaped thin body. As shown in FIG. 2, the board box 3 has a lowercase 10 and an upper case 11, and two light source boards 12 and a power terminal table 13 are accommodated in the board box 3.

Each of the light source board 12 is provided every light source unit 7, and has various kinds of circuits such as a power supply circuit for generating turn-on power for the light source unit 7, an LED drive circuit for controlling turn-on/off of LED, etc. The power supply terminal table 13 is a terminal table for connecting electric wires drawn from an electric wire take-in port (not shown) to electric wires extending from the light source boards 12.

The board box 3 is disposed on the bottom surface of the light source device 1, and the light source units 7, the light converging type light guide unit 8 and the holder unit 9 are assembled to the upper surface 11A of the board box 3.

A front cover 4 and a back cover 5 are designed as rectangular plate members which are provided to both the ends of the board box 3, respectively. Amount cavity 4 is formed in the surface of the front cover 4, and the light guide 2 is mounted in the mount cavity 14. The cover case 6 surrounds the space between the front cover 4 and the back cover 5, and the case body of the light source device 1 having a substantially rectangular parallelepiped shape is constructed by the front cover 4, the back cover 5 and the cover case 6. As not shown in FIG. 2, an exhaust port is formed in the surface of the back cover 5 so as to face the heat radiation fan 15.

The two light source units 7 are light sources of the light source device 1, and each of the light source units 7 has LED 2 as an example of a light emitting element, an LED board 21 on which the LED 2 is mounted, and a heat radiation unit 22 provided to the back surface of the LED board 21. The light source unit 7 makes light emitted from LED 20 incident to the light converging type light guide unit 8.

The LED board 21 comprises an aluminum board having high thermal conductivity, for example. The LED board 21 is designed to be substantially rectangular, and LED 20 is mounted substantially at the center of the mount face of the LED board 21. LED 20 is a so-called display surface mount type (SMD: Surface Mount Device) LED package obtained by sealing an LED chip in a case body 23 of 1.2 cm square with resin 24, and the optical axis K thereof is set to be substantially vertical to the mount surface of the LED board 21.

The two light source units 7 are secured to the upper surface 11A of the board box 3 so as to be erected substantially vertically to the upper surface 11A, and arranged so that the optical axes K of the respective LEDs 20 are substantially parallel to the upper surface 11A and intersect each other at 90°.

These light source units 7 are controlled to be turned on by the LED drive circuit provided to the light source board 12. In the light source device 1, both or only one of the two light source units can be turned on. An element having a proper light emission wavelength is selected as LED of the light source unit 7 in accordance with intended use of an endoscope or the material of the light guide 2. Elements having different light emission wavelengths may be used as LEDs 20 of the two light source units 7. For example, white LED for emitting white light and near infrared light LED for emitting near infrared light are used as LEDs 20 of the light source devices 1.

The heat radiation unit 22 is a member which is provided to the back surface of the LED board 21 and radiate heat of LED 20 at the mount surface side through the LED board 21, and has many heat radiation fins 22A extending substantially vertically from the back surface of the LED board 21. These heat radiation fins 22A are provided over substantially the whole surface of the LED board 21.

Ventilation ports 25 are provided in the upper surface 11A of the board box 3 so as to be located just below the heat radiation fins 22A of the heat radiation units 22, and the hat radiation fins 22A are cooled by air blown out from the ventilation port 25. The air blown from the ventilation port 25 is introduced from the front surface of the light source device 1. That is, air-intake ports 26 are formed in the surface of the front cover 4 at places nearer to the lower end of the front cover 4, that is, at places corresponding to the front surface of the board box 3. As shown in FIG. 2, the board box 3 has an open front surface, whereby outside air can be introduced through the air-intake ports 26 into the board box 3. A heat radiation fan 15 for exhausting inside air of the light source device 1 from the back cover 5 is disposed between the back cover 5 and one of the heat radiation units 22. Accordingly, outside air is taken from the air-intake ports 26 into the board box 3 by the exhaust operation of the heat radiation fan 15, and blown from the ventilation port 25 of the upper case 11 to the heat radiation fins 22A. When the outside air passes through the board box 3, the light source boards 12 in the board box 3 is also cooled by the air.

The light converging type light guide unit 8 combines respective light components of the light source units 7, and makes the combined light incident to the holder unit 9. The construction thereof will be described later.

Figure 3:
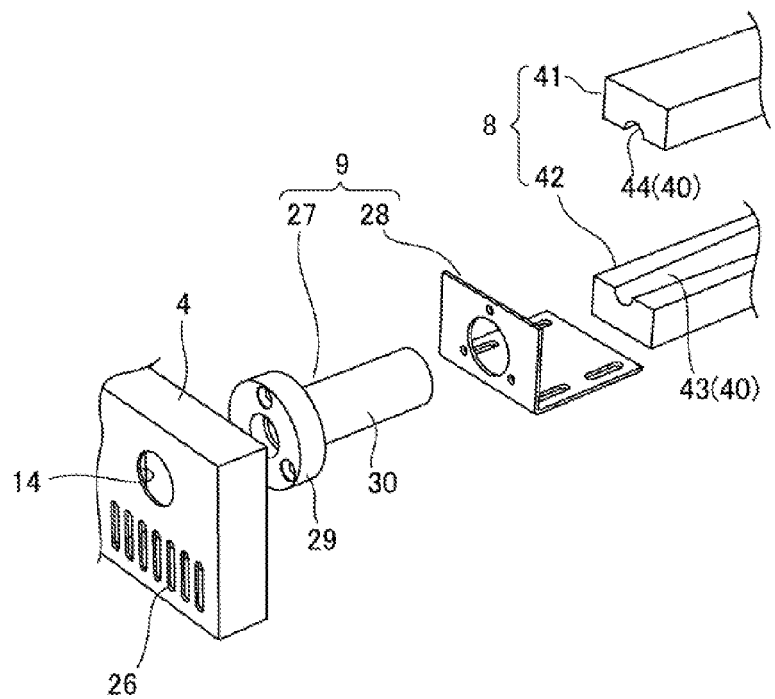
FIG. 3 is an exploded perspective view showing a holder unit.

FIG. 3 is an exploded perspective view showing the holder unit 9.

The holder unit 9 has a light guide holder 27 and a holder fixing clasp 28. The light guide holder 27 serves to hold the light guide 2 and position the light guide 2 to the emission end (a second focal point f2 described later in FIG. 4) of the light converging type light guide unit 8, and has a fitting flange 29 and a holding cylinder 30. The fitting flange 29 is disposed to face the mount cavity 14 of the front cover 4, and fitted to a fitting piece 31 (FIG. 1) provided to the tip portion of the light guide 2. The holding cylinder 30 holds the light guide 2 while a tip portion of the light guide 2 which is located at the front side of the fitting piece 31 of the light guide 2 is inserted in the holding cylinder 30. When the light guide holder 27 locks the light guide 2, an incidence end face 32 (FIG. 4) at the tip of the light guide 2 is positioned to the second focal point F2 of the light converting type light guide unit 8. The holder fixing clasp 28 is fixed to the board box 3 to support the holding cylinder 30 of the holder unit 9.

Figure 4:
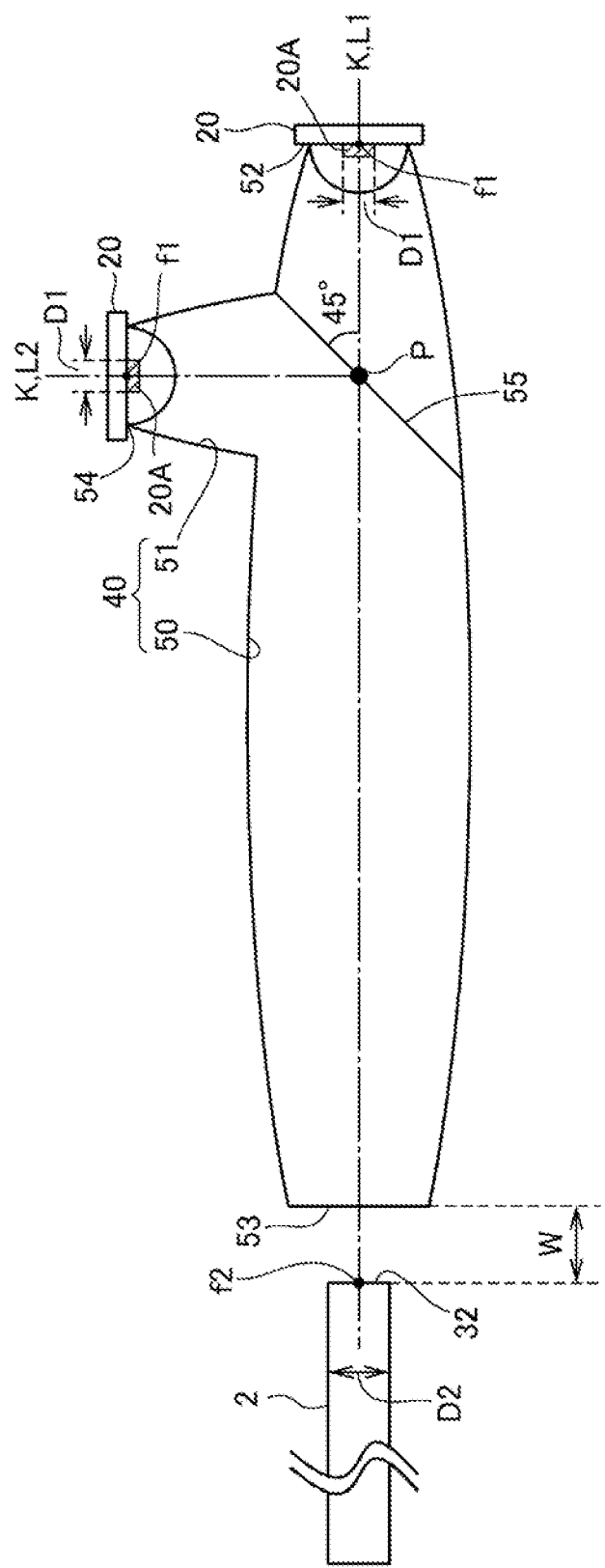
FIG. 4 is a diagram showing the construction of a light converging type light guide unit.

FIG. 4 is a diagram showing the construction of the light converging type light guide unit 8.

As described above, the light converging type light guide unit 8 combines respective light components from the two light source units, and applies the combined light components to the light guide 2 held by the holder unit 9. The light converging type light guide unit according to this embodiment is constructed by an optical condenser having a reflection face 40. Specifically, the light converging type light guide unit 8 has a pair of plate members which are joined to each other in the up-and-down direction as shown in FIG. 2. Concave portions 43, 44 are formed on the respective joint faces of the plate members 41, 44 respectively, and these concave portions 43, 44 are joined to each other to construct the reflection face 40 shown in FIG. 4. The light converging type light guide unit 8 is fixed to the upper surface 11A of the board box 3 by fixing clasps 45.

The reflection face 40 serves as a light converging optical system for converging light of each LED of the two light source units 7 to the incidence end face 32 of the light guide 2, and it surrounds the overall area from each LED 20 to a place in the neighborhood (the front side) of the incidence end face 32 of the light guide 2.

Specifically, the reflection face 40 has a slender cylindrical main reflection face 50 and a cylindrical sub reflection face 51 which extends substantially vertically from the side surface of the main reflection face 50. LED 20 as a light source is disposed at the end portion of each of the main reflection face 50 and the sub reflection face, and the light components of the respective LEDs 20 are combined with each other by the reflection face 40, and the combined light components are emitted from the end portion of the main reflection face 50.

The main reflection face 50 is a light converging reflection face whose long axis is set to the optical axis L1. That is, both the ends of the main reflection face 50 which are opened and located on the optical axis L1 are formed as a light source side opening 52 and a light-receiving side opening 53, and light emitted from the light source side opening 52 is converged to the light-receiving side opening 53. In this light source device 1, LED 20 is disposed at the light source side opening 52 (opening size D3: see FIG. 7), and the incidence end face 32 of the light guide 2 is disposed to be away from the light-receiving side opening from the distance W. Accordingly, light of LED 20 is converged and incident to the incidence end face 32 of the light guide.

The sub reflection face 51 has an open end portion, and formed as a light source side opening 54 at which the other LED 20 is disposed. The optical axis L2 of the sub reflection face 51 is set to intersect vertically to the optical axis L1 of the main reflection face 50. A dichroic mirror 55 is provided at the cross-point between the optical axis L1 and the optical axis L2 so as to be located on the optical axis L1 of the main reflection face 50 and tilted at an incident angle of 45°, and the light from the sub reflection face 51 is combined with the light from the main reflection face 50 by the dichroic mirror 55. The sub reflection mirror 51 is configured to be geometrically equivalent to a part of the main reflection face 50 which is located in the area from the cross point P of the dichroic mirror 55 to the light source side opening 52 (that is, a first focal point f1 described later). That is, the light of LED 20 disposed at the light source side opening 54 of the sub reflection face 51 is geometrically equivalent to the light of LED 20 disposed at the light source side opening 52 of the main reflection face 50. Accordingly, the light of LED 20 at the sub reflection face 51 side is also converged and incident to the incidence end face 32 of the light guide 2.

Figure 5:
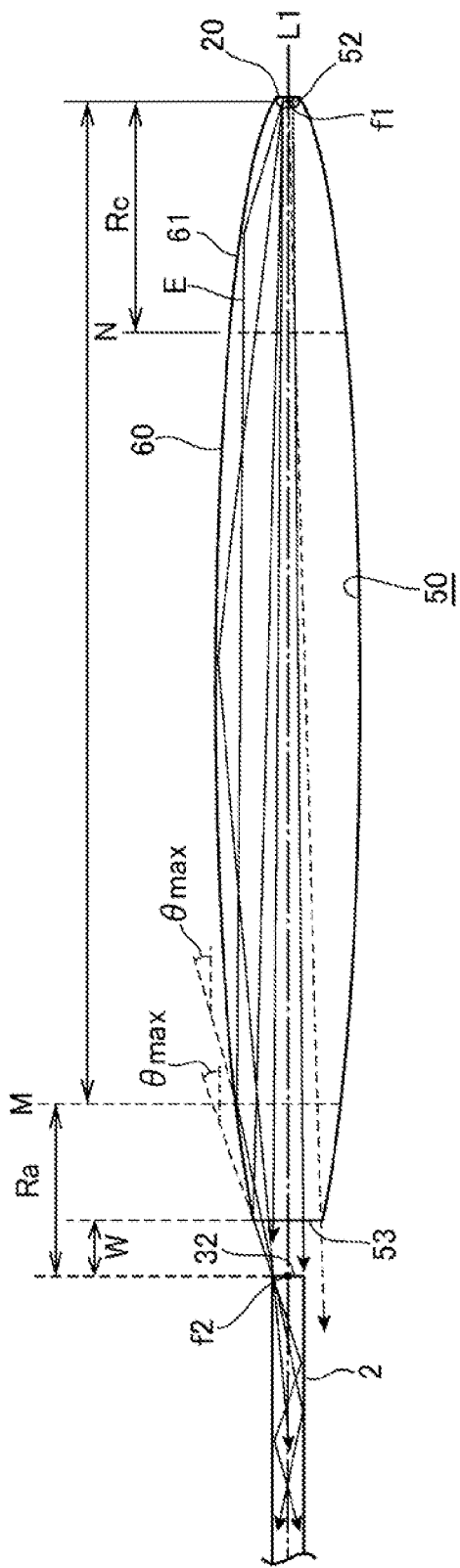
FIG. 5 is an optical path diagram of reflection light from a main reflection face.

FIG. 5 is an optical path diagram of reflection light of the main reflection face 50.

Since the sub reflection face 51 is geometrically equivalent to the main reflection face 50 in the area from the cross-point P of the dichroic mirror 55 to the light source side opening 52 (the first focal point f1) as described above, the reflection face 40 of the light converging type light guide unit 8 is geometrically equivalent to the main reflection face 50, and thus FIG. 5 can be regarded as an optical path diagram of the reflection face 40.

Figure 6:
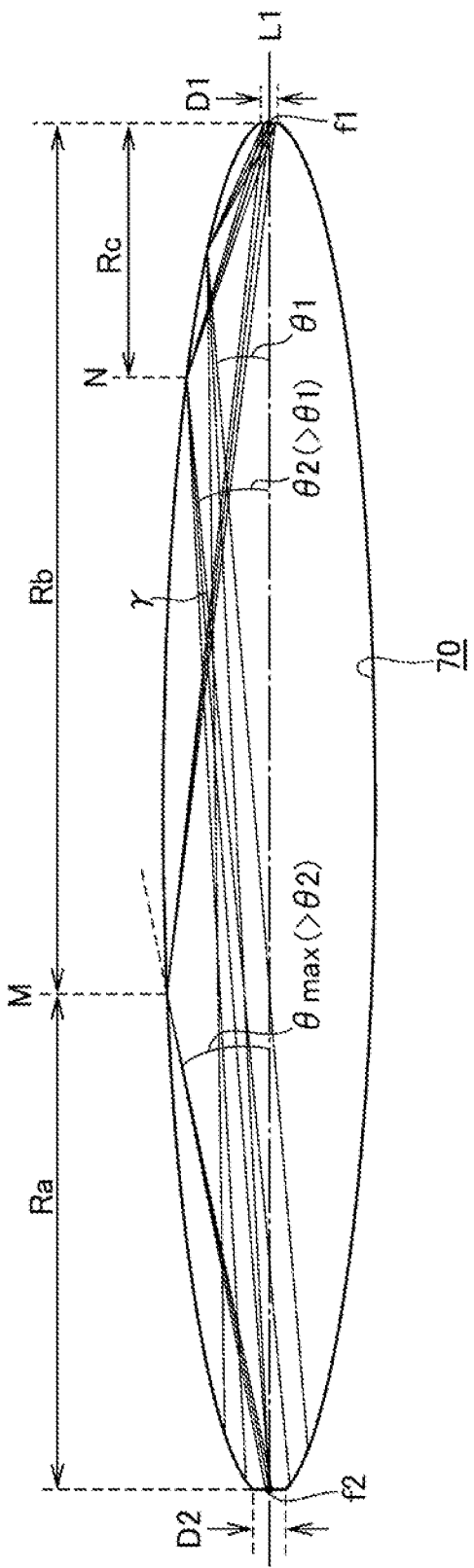
FIG. 6 is an optical path diagram when the main reflection face is constructed by an elliptical reflection face.

As described above, the main reflection face 50 is a light converging reflection face for converging light emitted from the light source side opening 52 to the light-receiving side opening 53. In general, an elliptical reflection face is known as a reflection type optical system for converging light of a light emission point to a light reception point. That is, as shown in FIG. 6, an elliptical reflection face 70 has two focal points of a first focal point f1 and a second focal point f2, and light emitted at the first focal point f1 is converged to the second focal point f2. The light emission point 20A of LED 20 is disposed at the first focal point f1, and the incidence end face 32 of the light guide 2 is disposed at the second focal point f2, whereby light emitted from LED 20 is converged to the incidence end face 32.

In order to guide light incident to the light guide 2 through the light guide 2, it is necessary that the incidence angle θ of the incident light is equal to the maximum incidence angle θmax=Arcsin (NA) or less when NA represents the numerical aperture of the light guide 2.

However, on the elliptical reflection face 70, the incidence angle θ of reflection light traveling to the second focal point f2 increases as light is reflected from a place which is farther away from the first focal point f1 (a place which is nearer to the second focal point f2) as shown in FIG. 6. That is, even when all the light reflected from the elliptical reflection face 70 is converged and incident to the incidence end face of the light guide 2, reflection light incident to the incidence end face at an incident angle θ which is equal to the maximum incidence angle θmax or more cannot be guided through the light guide 2 and thus this reflection light wastes.

Accordingly, when a point at which the incidence angle θ of the reflection light is equal to the maximum incidence angle θmax on the elliptical reflection face 70 is represented by a point M, a reflection area Ra from the point M to the second focal point f2 does not contribute to illumination light of the light guide 2, and thus this area becomes a needless area.

Particularly, as the numerical aperture NA of the light guide 2 decreases, the maximum incidence angle θmax is smaller, and the point M approaches to the first focal point f1 side. Accordingly, with respect to a reflection face extending from the first focal point f1 to the second focal point f2 like the main reflection face 50, as the numerical aperture NA of the light guide 2 decreases, the occupation rate of the needless reflection area Ra increases, and this is wasteful.

The light emission point of LED 20 is not a point, but has some size D1. Therefore, as shown in FIG. 6, reflection light traveling to the second focal point f2 spreads at an angle γ in accordance with the size D1 of the light emission point 20A, and light components deviating from the second focal point f2 occur. However, even when the reflection light spreads at an angle γ, the reflection light would be incident to the light guide 2 if the reflection light enters the range of the opening size D2 of the incidence end face 32 of the light guide 2. However, the deviation from the second focal point f2 caused by the spread of light is greater as the light is reflected from a place remoter from the second focal point f2, that is, the light is reflected from a place nearer to the first focal point f1. With respect to the elliptical reflection face 70, a point N at which reflection light contains light components deviating from the range of the opening size D2 is determined on the basis of the size D1 of the light emission point, the opening size D2 and the distance from the first focal point f1 to the second focal point f2. Accordingly, on the elliptical reflection face 70, a part of reflection light reflected from a reflection area Rc from the first focal point f1 to the point N deviates from the incidence end face 32 of the light guide, and thus it wastes.

Particularly, as the opening size D2 of the incidence end face 32 of the light guide 2 decreases, the point N approaches to the second focal point f2, so that the occupation rate of the reflection area Rc increases and this is wasteful.

As described above, assuming that the overall main reflection face 50 is constructed by the elliptical reflection face 70, there would be a problem that there is a lot of reflection light containing light components which are not guided through the light guide 2 or are not incident to the light guide 2. This problem is more remarkable as the numerical aperture NA of the light guide 2 is smaller, the opening size D2 of the incidence end face 32 of the light guide 2 decreases and/or the size D1 of the light emission point 20A is larger as described above.

In general, with respect to the endoscope, the directivity of illumination light is more greatly enhanced and a narrower range can be illuminated as the numerical aperture NA of the light guide 2 is smaller. Therefore, a light guide having the numerical aperture NA ranging from 0.2 to 0.35 (maximum incidence angle θmax=11.5° to 20°) and the opening size D2 of about 4 mm is used in the above light source device 1. Therefore, the numerical aperture NA and the opening size D2 are smaller than those of a general light guide. Furthermore, in this light source device 1, the light emission point 20A of LED 20 has a size D1 of 1 to 2 mm, and thus the above problem would remarkably occurs unless no countermeasure is taken.

Therefore, in the light source device 1, the main reflection face 50 is not configured merely as an elliptic reflection face 70, but configured to have the following construction.

That is, as shown in FIG. 5, with respect to the main reflection face 50, the reflection face from the point N to the second focus point f2 is configured as an elliptic reflection face 60. Furthermore, the reflection area Rc from the first focal point f1 to the point N is configured as a hyperbolic reflection face 61. That is, the main reflection face 50 is configured as a composite elliptic mirror in which the reflection area Rc from the first focal point f1 to the point N on the elliptic reflection face 60 is formed as the hyperbolic reflection face 61.

Figure 7:
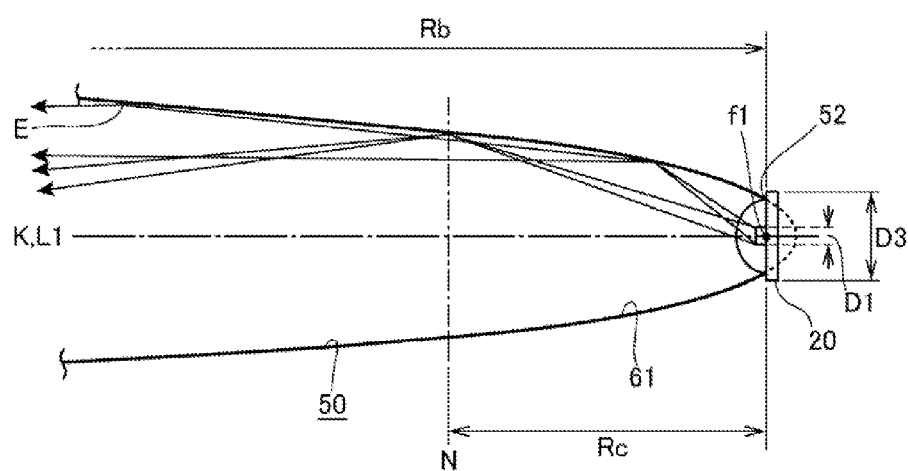
FIG. 7 is a diagram showing an optical path at a first focal point side of the main reflection face.

As shown in FIGS. 5 and 7, the hyperbolic reflection face 61 obtains reflection light E traveling in the direction to the second focal point f2 by using reflection of reflection light therefrom (primary reflection light) from the elliptical reflection face 70 (secondary reflection light). The hyperbolic reflection face 61 is designed so as to make light incident to the reflection area Ra so that reflection light E from the elliptical reflection face 70 is converged within the range of the opening size D2 of the light guide 2 and incident to the incidence end face 32 of the light guide 2 at the maximum incidence angle θmax or less. Furthermore, the hyperbolic reflection face 61 is also designed so that the reflection light E based on the secondary reflection light from the elliptical reflection face 70 can be also obtained by reflection from the reflection area Ra as shown in FIG. 5 to effectively use the reflection area Ra.

Accordingly, the reflection light (primary reflection light) from the reflection area Rc becomes the reflection light E which travels in the direction to the range of the opening size D2 of the light guide 2 at the maximum incidence angle θmax or less by the reflection from the elliptical reflection face 70. As a result, a lot of reflection light from the reflection area Rc can be made incident to the light guide 2, and the use efficiency of light emitted from LED 20 can be enhanced. Light which is emitted from LED 20, primarily reflected from the elliptical reflection face 60 and then converged to the second focal point f2 is omitted from FIG. 8. The sub reflection face 51 is geometrically equivalent to the main reflection face 50 from the cross-point P of the dichroic mirror 55 to the first focal point f1. That is, the reflection area Rc from the first focal point f1 of the sub reflection face 51 to the point N is configured as the hyperbolic reflection face 61 like the main reflection face 50.

Figure 8:
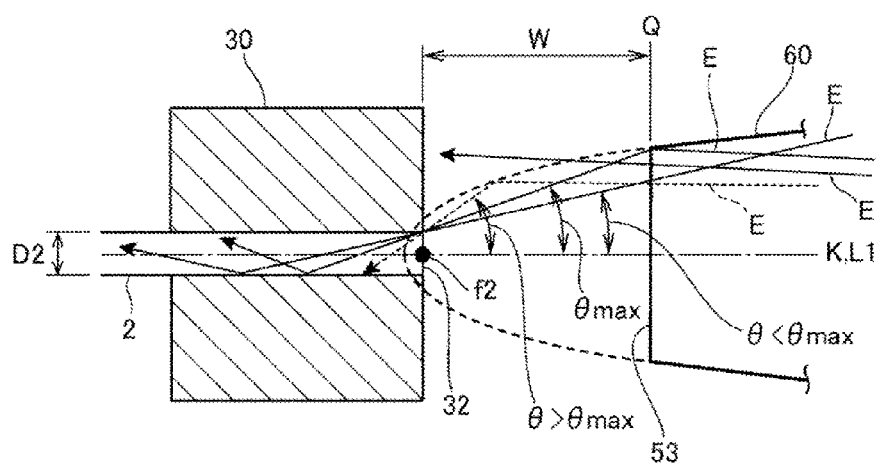
FIG. 8 is a diagram showing an optical path at a second focal point side of the main reflection face.

Here, as shown in FIG. 8, with respect to the reflection light E which is secondarily reflected from the elliptical reflection face 60, the incidence angle θ of the reflection light E to the incidence end face 32 increases as the reflection light E is reflected from a place nearer to the second focal point f2, and the incidence angle θ exceeds the maximum incidence angle θmax in the neighborhood of the second focal point f2. Such secondarily-reflected reflection light E is not guided through the light guide 2 even when it is incident to the light guide 2, and it becomes needless light. Therefore, in the light converging type light guide unit 8, the elliptical reflection face 60 is not designed to extend to the second focal point f2, but a light-receiving side opening 53 is provided in front of the second focal point f2, whereby reflection light E having the incidence angle which is equal to the maximum incidence angle θmax or more is not needlessly incident to the incidence end face of the light guide 2.

The distance W from the second focal point f2 (the position of the incidence end face 32 of the light guide 2) to the light-receiving side opening 53 is defined by a point Q at which the incidence angle θ of the reflection light E based on the secondary reflection exceeds the maximum incidence angle θmax. However, it is needless to say that the elliptical reflection face 60 may be designed to extend to the second focal point f2 in this light converging type light guide unit 8.

Figure 9:
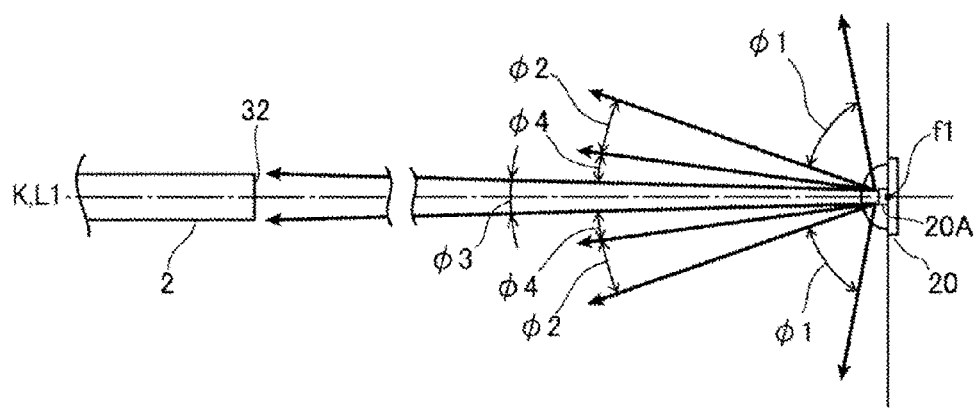
FIG. 9 is a diagram showing light flux of LED which is incident to a light guide to be wave-guidable.

Here, a light flux traveling to the neighboring hyperbolic reflection face 61 is represented by a light flux φ1, a light flux converged to the second focal point f2 due to the primary reflection from the elliptical reflection face 60 is represented by a light flux φ2, and a light flux which is directly incident to the light guide 2 is represented by a light flux φ3. According to the thus-constructed main reflection face 50, as shown in FIG. 9, the light fluxes φ1, φ2 and φ3 out of radiation light of LED 20 are incident to the incidence end face 32 of the light guide 2 at the maximum incidence angle θmax. Only a light flux φ4 in the range between the light flux φ3 and the light flux φ2 is incident to the incidence end face 32 at an angle exceeding the maximum incidence angle θmax, or deviates from the range of the incidence end face 32.

As described above, most of the light fluxes φ1, φ2 and φ3 excluding the light flux φ4 of LED 20 can be converged and incident to the light guide 2 by using the main reflection face 50 described above, so that the radiation light of LED 20 can be very efficiently used.

In the light source device 1, the numerical aperture NA of the light guide 2 is set to 0.2, the maximum incidence angle θmax=11.5°, the opening size D2 is set to 4 mm, and the size of the light emission point 20A of LED 20 is set to 1.2 mm, for example. With respect to the main reflection face 50, the distance between the first focal point f1 and the second focal point f2 is set to 150 mm, the light source side opening 52 is set to 1.2 mm which corresponds to the size D1, and the light-receiving side opening 53 is set to 4 mm which corresponds to the opening size D2.

As described above, according to this embodiment, the elliptical reflection face 60 is formed at the second focal point f2 side of the main reflection face 50 while the hyperbolic reflection face 61 is formed at the first focal point f1 side of the main reflection face 50. Therefore, even when the light emission point 20A of LED 20 has a size D1, light reflected from a place near to the first focal point f1 (the reflection area Rc in FIG. 5) can be efficiently made incident to the incidence end face 32 of the light guide 2.

Furthermore, with respect to the reflection light reflected from the reflection area Ra in the neighborhood of the incidence end face 32 of the elliptical reflection face 60, the incidence angle to the incidence end face 32 of the light guide 2 can be controlled. Therefore, the reflection light can be made incident to the incidence end face 32 at the maximum incidence angle θmax or less, and incidence light which is not guided through the light guide 2 and thus wastes can be reduced.

According to this embodiment, the hyperbolic reflection face 61 is formed in the reflection area Rc in which reflection light deviating from the incidence end face 32 of the second focal point f2 would occur due to the size of LED 20 on the assumption that the overall main reflection face 50 is designed as the elliptical reflection face 70. Accordingly, a lot of light which deviates from the incidence end face 32 due to the size D1 of the light emission point 20A of LED 20 can be made incident to the light guide 2.

Furthermore, according to this embodiment, the main reflection face 50 is configured to extend from the light emission point 20A of LED 20 to a place in the neighborhood of the incidence end face 32 of the light guide 2 and surround the space therebetween. Therefore, the light emitted from LED 20 can be guided to the light guide 2 while substantially contained, the use efficiency of LED 20 can be enhanced, and disturbance light to the light guide 2 can be enhanced.

According to this embodiment, the dichroic mirror 55 is provided on the optical axis L1 of the main reflection face 50, and the main reflection face 50 is configured to have the sub reflection face 51 which is geometrically equivalent to the face extending from the dichroic mirror 55 to the first focal point f1 of the main reflection face 50. Furthermore, LED 20 is disposed at the first focal point f1 of the sub reflection face 51, and light at the sub reflection face 51 side and light at the main reflection face 50 side are combined with each other by the dichroic mirror 55.

Accordingly, the output light amount can be increased. Furthermore, output light obtained by mixing plural emission light colors can be simply obtained by changing the color of light emitted from one of the LEDs 20.

The present invention is not limited to the above embodiments, and any modification and any application may be made to the above embodiments without departing from the subject matter of the present invention.

For example, in the above embodiments, the hyperbolic reflection face is adopted at the first focal point f1 (the light emission point 20A) side of the main reflection face 50. However, the present invention is not limited to this style. That is, any curved surface (face) may be adopted insofar as it reflects light of LED 20 to the reflection area Ra of the elliptical reflection face 60 so that the light travels in the direction to the incidence end face 32 of the light guide 2 and is incident to the incidence end face 32 at the maximum incidence angle θmax or less by the reflection from the reflection area Ra.

Furthermore, in the above embodiment, the reflection face 40 is configured so that the dichroic mirror 55 is provided on the optical axis L1 of the main reflection face 50 and light components from two LEDs 20 are combined with each other. However, the present invention is not limited to this style. For example, three or more light components may be combined with one another by using a dichroic prism or the like in place of the dichroic mirror 55. Furthermore, the reflection face 40 maybe constructed by only the main reflection face 50 without providing the sub reflection face 51 to the reflection face 40.

Figure 10:
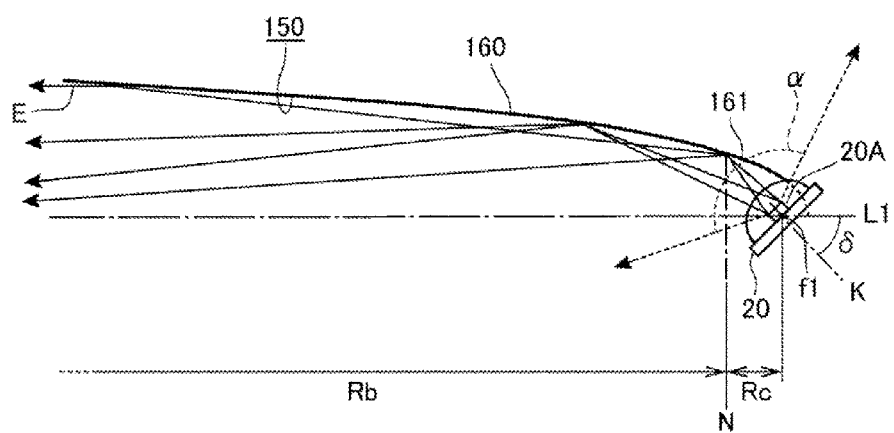
FIG. 10 is a diagram showing a main reflection face according to a modification of the present invention.

Furthermore, in the above embodiment, LED 20 is provided on the main reflection face 50 so that the optical axis K of the LED 20 is coincident with the optical axis L1 of the main reflection face 50. However, the present invention is not limited to this style. For example, as shown in FIG. 10, LED 20 may be disposed so that the optical axis L1 of the main reflection face 150 and the optical axis K of LED 20 intersect to each other at a predetermined angle δ. In this case, a curved surface reflection face 161 is formed at the place corresponding to the reflection area Rc described above on the main reflection face 150, and an elliptical reflection face 160 is formed at the other place. The tilt angle δ of LED 20 with respect to the optical axis L1 of the main reflection face 150 is determined so that a large amount of light flux in a light emission range α of LED 20 can be reflected from the main reflection face 150 and incident to the light guide 2.

The light converging type light guide unit may be configured to have only one of two parts (upper and lower parts in FIG. 10) into which the main reflection face 150 is divided along the optical axis L1, the one part intersecting to the optical axis K of LED 20.

Furthermore, the light source is not limited to LED 20, and it is preferably as close to a point light source as possible. LEDs 20 of the main reflection face 50 and the sub reflection face 51 may be configured to be different in output power and/or emitted light color.

What is claimed is:

1. A light converging type light guide unit that guides light emitted from a light source to an incidence end face of a light guide that is disposed at a light reception point, extends linearly, has one end facing the incidence end face of the light guide and an other end at which a light emission point of the light source is disposed, and comprises a reflection face that extends from the one end to the other end, wherein
the reflection face comprises:
an elliptical reflection face that is disposed at a side of the one end of the reflection face and that has a first focal point at which the light emission point is disposed and a second focal point at which the light reception point is disposed, and the elliptical reflection face comprises a reflection area that is disposed at the second focal point side of the elliptical reflection face,
the reflection area is configured to primary reflect direct light from the light emission point incident toward the second focal point with an incidence angle of more than Arcsin (numerical aperture NA of the light guide that is disposed at the light reception point), and
a curved surface reflection face that is disposed at a side of the other end of the reflection face and that is shaped to primary reflect direct light from the light emission point incident toward the reflection area of the elliptical reflection face, and to make primary reflected light from the curved surface reflection face be secondary reflected at the reflection area of the elliptical reflection face incident to the light reception point with an incidence angle of equal to Arcsin (numerical aperture NA of the light guide that is disposed at the light reception point) or less.

2. The light converging type light guide unit according to claim 1, wherein the curved surface reflection face is provided in an area of the reflection face where reflection light deviating from the incidence end face of the light guide would occur due to a size of the light emission point.

3. The light converging type light guide unit according to claim 1, further comprising a dichroic mirror provided on an optical axis of the reflection face, wherein the reflection face has a sub reflection face which is geometrically equivalent to a face extending from the dichroic mirror to the first focal point, a light emission point of a second light source is disposed at a first focal point of the sub reflection face, and light from the second light source at the sub reflection face side and light from the light source at the reflection face side are combined with each other by the dichroic mirror.

4. The light converging type light guide unit according to claim 2, further comprising a dichroic mirror provided on an optical axis of the reflection face, wherein the reflection face has a sub reflection face which is geometrically equivalent to a face extending from the dichroic mirror to the first focal point, a light emission point of a second light source is disposed at a first focal point of the sub reflection face, and light from the second light source at the sub reflection face side and light from the light source at the reflection face side are combined with each other by the dichroic mirror.

5. A light source, comprising:
a holder unit that holds a light guide, and
a light converging type light guide unit that extends linearly, has an one end facing the incidence end face of the light guide and an other end at which a light emission point of the light source is disposed, and comprises a reflection face that extends from the one end to the other end, wherein
the reflection face comprises:
an elliptical reflection face that is disposed at a side of the one end of the reflection face and that has a first focal point at which the light emission point is disposed and a second focal point at which the light reception point is disposed, and the elliptical reflection face comprises a reflection area that is disposed at the second focal point side of the elliptical reflection face,
the reflection area is configured to primary reflect direct light from the light emission point incident toward the second focal point with an incidence angle of more than Arcsin (numerical aperture NA of the light guide that is disposed at the light reception point), and
a curved surface reflection face that is disposed at a side of the other end of the reflection face and that is shaped to primary reflect direct light from the light emission point incident toward the reflection area of the elliptical reflection face, and to make primary reflected light from the curved surface reflection face be secondary reflected at the reflection area of the elliptical reflection face incident to the light reception point with an incidence angle of equal to Arcsin (numerical aperture NA of the light guide that is disposed at the light reception point) or less.

6. The light source according to claim 5, wherein the curved surface reflection face is provided in an area of the reflection face where reflection light deviating from the incidence end face of the light guide would occur due to a size of the light emission point.

7. A light converging type light guide unit that guides light emitted from a light source to an incidence end face of a light guide that is disposed at a light reception point and has an opening size, extends linearly, has one end facing the incidence end face of the light guide and an other end at which a light emission point of the light source is disposed, and comprises a reflection face that extends from the one end to the other end, wherein
the reflection face comprises:
an elliptical reflection face that is disposed at a side of the one end of the reflection face and that has a first focal point at which the light emission point is disposed and a second focal point at which the light reception point is disposed, and
a curved surface reflection face that is disposed at a side of the other end of the reflection face,
the reflection face further comprising an reflection area at which direct light from the light emission point is reflected to be reflected light that deviates from the opening size of the incident end face in case that a whole of the reflection face is configured with the elliptical reflection face,
the reflection area extends from the other end of the reflection face to a point that is determined on a basis of a size of the light emission point, the opening size and the distance from the first focal point to the second focal point,
the elliptical reflection face extends from the one end of the reflection face to the point, and comprises a reflection area that is disposed at the one end side of the elliptical reflection face,
the reflection area is configured to primary reflect the direct light from the light emission point incident toward the light reception point with an incidence angle of more than Arcsin (numerical aperture NA of the light guide that is disposed at the light reception point),
the curved surface reflection face is disposed at an area corresponds to the reflection area, and is shaped to primary reflect direct light from the light emission point incident toward the reflection area of the elliptical reflection face, and to make primary reflected light from the curved surface reflection face be secondary reflected at the reflection area incident to the light reception point with an incidence angle of equal to Arcsin (numerical aperture NA of the light guide that is disposed at the light reception point) or less.

* * * * *